(12) United States Patent
Maschke (10) Patent No.: US 7,592,600 B2
(45) Date of Patent: Sep. 22, 2009

(54) DIAGNOSIS DEVICE FOR RADIOGRAPHIC AND NUCLEAR MEDICAL EXAMINATIONS

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 238 days.

(21) Appl. No.: 11/598,189

(22) Filed: Nov. 9, 2006

(65) Prior Publication Data
US 2007/0102645 A1 May 10, 2007

(30) Foreign Application Priority Data
Nov. 10, 2005 (DE) .................. 10 2005 053 994

(51) Int. Cl.
*H01L 27/146* (2006.01)
*G01T 1/20* (2006.01)
(52) U.S. Cl. .................. 250/370.09; 250/370.11
(58) Field of Classification Search ............ 250/370.09, 250/370.11
See application file for complete search history.

(56) References Cited

U.S. PATENT DOCUMENTS

| 5,638,817 | A | 6/1997 | Morgan et al. |
| 5,719,400 | A | 2/1998 | Cherry et al. |
| 5,752,513 | A | 5/1998 | Acker et al. |
| 6,661,240 | B1 | 12/2003 | Johnson et al. |
| 6,934,352 | B2 | 8/2005 | Freytag et al. |
| 7,332,724 | B2* | 2/2008 | Hefetz et al. ........... 250/370.06 |
| 2002/0163994 | A1 | 11/2002 | Jones |
| 2003/0014132 | A1 | 1/2003 | Ohba et al. |
| 2004/0100557 | A1 | 5/2004 | Roberts et al. |
| 2005/0027187 | A1 | 2/2005 | Barth et al. |
| 2007/0208327 | A1* | 9/2007 | Rosemberg et al. ........... 606/11 |
| 2008/0281181 | A1* | 11/2008 | Manzione et al. ........... 600/407 |

FOREIGN PATENT DOCUMENTS

| DE | 102 37 347 B4 | 3/2004 |
| DE | 103 33 543 A1 | 2/2005 |
| EP | 1 034 738 A1 | 9/2000 |
| WO | WO 2004/095069 A1 | 11/2004 |

OTHER PUBLICATIONS

Zhengjun Liu, S. Melvyn Lobo, Stanley Humphries, Clare Horkan, Stephanie A. Solazzo, Andrew U. Hines-Peralta, Robert E. Lenkinski, S. Nahum Goldberg,"Radiofrequency Tumor Ablation: Insight into Improved Efficacy Using Computer Modeling", AJR: 184, Apr. 2005, pp. 1347-1352.

(Continued)

*Primary Examiner*—David P Porta
*Assistant Examiner*—Mindy Vu (57) ABSTRACT

The invention relates to a diagnosis device which is proposed for combined or combinable radiographic and nuclear medical examinations comprising: an x-ray source, an examination room for accommodating a patient, a gamma radiation source arranged in the body of the patient, a detector system which has a detector surface for simultaneously measuring the x-ray and gamma radiation without changing the patient's position or which is designed to record a two-dimensional locally-resolved and object-imaging individual x-ray projection image. The diagnosis device is designed to carry out the radiographic examination by evaluating the measurement of the x-rays and to carry out a single photon emission examination as a nuclear medical examination by evaluating the gamma radiation.

19 Claims, 6 Drawing Sheets

OTHER PUBLICATIONS

David W. Barker, Ronald J. Zagoria, Kathryn A. Morton, Peter V. Kavanagh, Perry Shen, "Evaluation of Liver Metastases After Radiofrequency Ablation: Utility of $^{18}$F-FDG PET and PET/CT", AJR: 184, Apr. 2005, pp. 1096-1102.

Michael D. Beland, Damian E. Dupuy, William W. Mayo-Smith, "Percutaneous Cryoablation of Symptomatic Extraabdominal Metastic Disease: Preliminary Results", AJR:184, Mar. 2005, pp. 926-930.

Jeong Min Lee, Joon Koo Han, Seung Hong Choi, Se Hyung Kim, Jae Young Lee, Kyung Sook Shin, Chang Jin Han, Byung Ihn Choi, "Comparison of Renal Ablation with Monopolar Radiofrequency and Hypertonic-Saline-Augmented Bipolar Radiofrequency: In Vitro and In Vivo Experimental Studies", AJR:184, Mar. 2005, pp. 897-905.

C. Weigel, S. Schuchmann, M. Kirsch, B. Mensel, N. Hosten, "Perkutane Laserablation von Lungenmetastasen, Indikatin, technische Durchführung, erste Ergebnisse und Bildbefunde", Der Radiologe 5, 2004, pp. 491-499, vol. 44, Springer-Verlag.

Timo Mäkelä, "Data Registration and Fusion for Cardiac Applications", Dissertation, 2003, pp. i-iii, 1-39, ISBN 951-22-6514-1, Helsinki University of Technology, Laboratory of Biomedical Engineering, Internet: http://lib.hut.fi/Diss/2003/isbn951226515X/.

Siemens AG, Medical Solutions, Henkestr. 127, D-91052 Erlangen, Germany, "Symbia, A Merger of True Equals", Data-Sheet, Order No. A91004-M2310-G042-2-7600, Jan. 11, 2004, pp. 1-24.

* cited by examiner

DIAGNOSIS DEVICE FOR RADIOGRAPHIC AND NUCLEAR MEDICAL EXAMINATIONS

CROSS REFERENCE TO RELATED APPLICATIONS

This application claims priority of German application No. 10 2005 053 994.7 filed Nov. 10, 2005, which is incorporated by reference herein in its entirety.

FIELD OF THE INVENTION

The invention relates to a diagnosis device for combined or combinable radiographic and nuclear medical examinations having an x-ray source, an examination room for accommodating a patient with a gamma radiation source arranged in the body, with the diagnosis device being designed in order to carry out the radiographic examination by evaluating the measurement of the x-rays and to carry out a single-photon-emission (SPE) examination as a nuclear medical examination by evaluating the gamma radiation.

BACKGROUND OF THE INVENTION

Digital imaging methods have now become common practice in medical diagnostics. Methods of this type have been used for some time, e.g. in computer tomography, for magnetic resonance examinations, ultrasound examinations and for nuclear medical methods.

Diagnosis devices known as SPECT (Single Photon Emission Computer Tomographs) which enable a functional imaging have been implemented over the last few years in the field of nuclear medicine. The method is based on the basis of a tracer-principle with radioactive substances. In this method, by adding a very small quantity of a radioactive marked compound into the object to be examined, the metabolism thereof is monitored by measuring the radioactive radiation from the outside, in other words in a non-invasive manner. The marked tracer accumulates in specific organs and/or tumors or metastases and thus permits a good diagnosis of the metabolism, the locating of tumors and metastases or also an evaluation of the perfusion of the myocardial muscle. With the SPECT, radionuclides (isotope) are used, which decay while emitting individual gamma quanta. Tracers used in SPECT are for instance Tc99m-MDP (Tc=Technetium) for bones, TI-201 or Tc99m-MIBI for Myocardial Perfusion or Iodine-131 in the case of thyroid tumors. Nuclear medical imaging uses the tracer principle by producing images of the distribution of the radioactivity of a tracer. The radioactive radiation is usually detected by way of scintillation detectors.

As is known, the SPECT technique does not provide good anatomical imaging, thereby rendering the localization of detected tumors or metastases in the body of the patient problematic for instance. To achieve a better anatomical imaging, the patient can be examined before or after the SPECT examination using a radiographic CT (Computed tomographs) or MRI (Magnetic Resonance imaging). The challenge which then presents itself is that of correct registration, namely to correctly overlay and jointly display the recordings of the SPECT and or the CT and/or MRI. To this end, the image data is transferred to a common coordinates system, with this method also being known as a "software based registration". Methods of this type are known for example from U.S. 2005/0027187 A1 or from the dissertation by Timo Mäelä entitled "Data Registration and Fusion for Cardiac Applications" ISBN 951-22-6514. The disadvantage of these types of registration methods is that they have to be carried out interactively after the examinations and they are restricted in their accuracy.

The SPECT (Single Photon Emission Computer Tomography) CT diagnosis device of the applicant Siemens AG, Erlangen, Germany, with the product name "Symbia", which will become the future state of the art, provides the opportunity of carrying out nuclear medical SPECT examinations and radiographic CT examinations consecutively, but nevertheless in a combined piece of equipment.

The publication WO 2004/095069 A1 discloses a detector element for the combined detection of x-rays and gamma radiation. This detector element has a converter, which generates a charge signal as a function of incident x-ray or gamma quanta. In an evaluation device which is arranged downstream, the charge signal is amplified and evaluated on two different branches, with the first branch comprising an individual pulse analyzer in order to determine information for PET (Positron Emission Tomography) and the second branch comprising a pulse sequence analyzer in order to determine information for CT (computer tomography).

SUMMARY OF THE INVENTION

The object underlying the invention is to propose a diagnosis method in order to improve accessibility to the patient.

This object is achieved by a device with the features of the claims. Preferred or advantageous embodiments are given by the description below and the features of the sub-claims.

The inventive diagnosis device is designed for a combined and/or combinable radiographic and nuclear medical examination, with the radiographic examination being designed in particular as an x-ray projection examination. The evaluations of both the radiographic and also the nuclear medical examinations preferably comprise digital imaging methods.

The diagnosis device comprises an x-ray source, which generates x-rays of the human body for examination purposes. The x-ray source is preferably designed as an x-ray tube, preferably having x-ray voltages from 120 to 150 kV, which, in particular, produce x-ray quanta with energy of approximately 100 keV.

Furthermore, an examination room is provided, which serves to accommodate a patient. For the nuclear medical examination and prior to the start of the examination, radioactive materials (tracers) are placed in the patient's body in the tissue/organ to be examined, with the aid of suitable radiopharmacs. These radiopharmacs and/or radioactive materials emit gamma radiation (high energy photons). The radiopharmacs mentioned in the introduction are typically used.

The energies of the x-ray quanta of the x-ray source and the energies of the gamma quanta preferably lie in a similar energy range, in particular from 80 to 160 keV and are thus of a physically similar nature. For distinction purposes, the expressions x-rays, x-ray quanta etc. within this application nevertheless always relate to photons, which are generated in the x-ray source and the expressions gamma radiation, gamma quanta etc. always relate to photons which are emitted by radioactive materials (tracers) placed within the body of the patient.

On the one hand, the diagnosis device is designed to carry out a classical radiographic examination, in other words an x-ray projection medical examination on the patient. On the other hand, the diagnosis device is designed to carry out a nuclear medical single-photon-emission (SPE) examination on the patient. In the case of the single-photon-emission (SPE) examination known per se, the gamma quanta emitted by the radioactive materials arranged in the body of the patient is detected in an integrating measurement.

The diagnosis device comprises a detector system, which, according to the first alternative embodiment as claimed in the claims is designed to simultaneously measure the x-rays and gamma radiation. The x-ray and gamma quanta can be detected using one and the same detector system, in particular using one and the same detector elements. The detector system preferably comprises a flat detection surface and/or a detection surface which is only slightly curved having a radius of curvature greater than the multiple, in particular greater than the threefold distance of the detection system from the central point of the examination room, with the measurement space of the detector system especially only penetrating the examination room without overlapping. In particular, the detection system does not have a detector arrangement, which is suitable for a PET (positron emission tomography) examination.

With the second alternative embodiment as claimed in the claims, provision is made that the detector system or a detector system for the radiographic examination is designed to record a two-dimensional locally-resolved and graphically imaging individual x-ray projection image. In contrast with the known CT devices, which have a detector array with one or a number of column sensors, the detector system according to the invention has a flat panel detector for instance, which allows a two-dimensional recording.

The idea underlying the invention is to reduce the system-specific space required for the diagnosis device by adjusting the system technology. The first alternative embodiment of the invention is provided to reduce the space requirement by economizing on detectors. With the second alternative, an examination based on x-ray projection images is carried out in place of the radiographic CT, thereby in this way particularly saving on the bulky annular construction (gantry) used for recording and on the rapid rotation of the detector and the x-ray source about the patient. Both alternatives to the invention are thus advantageous in that the patient is more easily accessible during the examination. The basis is thus established not only to examine but also to treat the patient in the diagnosis device.

In addition, it is advantageous that the diagnosis device contains all necessary elements of an SPE device and an x-ray device, but however also makes joint use of a plurality of components, such as an image computer, an image and data storage device, a DICOM data network interface, a patient table for instance, thus rendering it more cost-effective compared with two individual devices.

Furthermore, the first alternative embodiment of the invention is additionally advantageous in that the radiographic and the nuclear medical examination is carried out at the same position without changing the patient's position and a common measurement coordinates system is thus used. A subsequent coordinates transformation for overlaying the measurement results (fusion) of the nuclear medical and radiographic examination is not necessary since a "hardware based registration" exists as a result of the mutual measurement position.

The detector system is preferably designed as a flat panel detector with a sensor matrix and/or a pixel matrix and or comprises the above. Provision is made in particular for several sensors/pixels to be assigned to a common readout channel and/or a common analog/digital converter.

In a preferred embodiment, the flat panel detector features a readout matrix, in particular a TFT matrix, upstream of which is arranged a converter, which converts an incident high-energy photon, i.e. an x-ray or a gamma quanta, into an electrical charge or into a lower-energy light pulse. The converter is designed particularly as a scintillator.

In order to be able to avoid artifacts and mismeasurements, an optional collimator can be provided in particular as a scattered radiation filter, said collimator being designed as a directional filter for the high-energy photons, i.e. the x-ray and gamma quanta. Photons comprising a movement direction which is vertical or essentially vertical to a detector surface and/or to the converter are preferably admitted by the collimator.

A signal for each individual sensor and/or for each individual pixel can be advantageously output by the flat panel detector by means of an adjustable or controllable integration time, with the individual sensors and/or individual pixels being configured in particular as integrating elements.

In one possible embodiment, the diagnosis device features an SPE detector in a sequential arrangement and in particular a separate x-ray detector. Provision is preferably made for a patient table to be able to be introduced from the SPE detector side as well as from the x-ray detector side.

In one preferred embodiment, the diagnosis device is designed to produce 3D soft tissue images by evaluating the detected x-ray radiation. The diagnosis device is preferably designed as a sequential combination of SPE detector and x-ray detector, with the SPE detector being integrated into an angiographic x-ray diagnostics device for rotational angiography. In principle, the invention is based on the idea of combining anatomical imaging (radiography) with functional diagnostic (SPE). The last-mentioned embodiment additionally provides for at least partially carrying out the functional diagnostics by means of radiography. This method results in a dual identification of soft parts, in particular of metastases or tumors, so that the registration can be examined in a particularly simple manner.

A control and evaluation device is expediently provided, which supports different operation modes, namely in particular the insulated and/or combined and/or combinable use of SPE or SPECT or x-ray examination possibilities. In particular, a module for the data fusion of radiographic and nuclear medical measurement data is provided, which results in combined SPE/SPECT x-ray data sets. The data fusion is preferably carried out in real-time.

With a preferred embodiment, the diagnosis device comprises an integrated tumor treatment device and/or a device for minimally invasive patient treatment, which is and/or are coupled for control purposes to the control and evaluation device. The tumor treatment device is preferably designed as a laser ablation device. Alternatively, the tumor treatment device is designed as a radio frequency ablation device. Alternatively, the tumor treatment device is designed as a cryoablation device.

A movement sensor system is optionally provided to capture patient movements in the inventive diagnosis device. The patient movements are preferably recorded during the examination and/or during a transition period from a nuclear medical examination to the radiographic examination and are considered when fusing the measurement results. The control and evaluation device preferably comprises a module, which is designed to control the movement sensor system as well as to correct the nuclear medical and/or radiographic measurement data on the basis of the measured patient movements. The following embodiments are possible:

Movement sensor system with a mathematical movement sensor, which derives the patient movements from the image signals, in particular the measurement signals of the nuclear medical and/or radiographic examination.

Movement sensor system with a sensor having an electrical operation principle.

Movement sensor system with a capacitative operation principle.

Movement sensor system with a magnetic operation principle.

Movement sensor system with an acoustic operation principle.

Movement sensor system with an optical operation principle, e.g. by scanning using a laser beam or using an optical camera operating (in particular in the visible range) or in the infrared range.

The data of the movement sensor system is either transmitted to the control and evaluation device with a fixed link or wirelessly.

With a particularly preferred embodiment, the movement sensor system is designed in RFID transponder technology, and is equipped in particular with an RFID receiver system. Provision is preferably made for the RFID transmitter to be equipped with an adhesive surface and affixed to the patient in a manner similar to that of a plaster. In particular, the RFID transmitter is designed as a disposable article, which is disposed of after its use.

Optional sensors for measuring the ECG, breathing and vascular pulsation are provided to detect organ movements, such as for instance movements of the heart, the ribcage and the blood vessels. The measurement results are preferably forwarded to the control and evaluation device and taken into account with the image reconstruction and/or data fusion, and artifacts emanating therefrom are especially eliminated for instance by means of "gating".

A chest band can be used for instance to eliminate breathing artifacts, said chest band comprising sensors which are designed to record the breathing amplitude and/or frequency. Another option is to calculate the breathing amplitude and/or frequency from the ECG signal, in particular from an envelope curve of the ECG signal. In addition or alternatively, the pulse of the vessel is determined by evaluating the ECG or the blood pressure curve.

An advance system is preferably provided to move the patient through the measurement area of the detector system, said advance system allowing the patient to be advanced through the diagnosis device. In particular, the diagnosis device is designed to control the advance system and detector system in a synchronized manner.

With one development, the advance system comprises a position sensor which is designed to record the advance movement of the patient and is arranged for instance in a moveable examination table. The data of the position sensor, in particular the movement data of the patient and/or of the examination table, is preferably forwarded to the evaluation and control device and taken into account during the image reconstruction and/or data fusion.

With a preferred embodiment of the diagnosis device, a calibration module is preferably provided in the evaluation and control device, with the movement sensor system and/or the position sensor being calibrated in respect of the spatial coordinates of the diagnosis device.

It is advantageous if x-ray source and/or detector system are arranged opposite one another on the end segments of a C-arm-shaped bracket, which is rotatable such that the end segments describe circular paths about the patient arranged in the central point of the circular path. With one possible embodiment, the C-arm construction is accommodated by an industrial robot, preferably having five degrees of freedom. Alternatively, the x-ray source and detector system can be mounted on moveable stands, which are mounted for instance on the ceiling or the floor of a frame or of a treatment room, with the stands preferably being moveable in three degrees of freedom. A recording of this type is disclosed in U.S. Pat. No. 6,934,352 B2: "Method and Apparatus and Computer Program Product for determining an Abort Criterion during Acquisition of 2D Images of a 3D Subject", the disclosure of which is included by referencing to the present description.

With an advantageous development, the diagnosis device, in particular the evaluation and control device, is designed such that measurement data of the nuclear medical examination and the radiographic examination is temporarily offset, and/or can be read out and/or is read out alternately from the detector system and/or the detectors. In particular, the readout process is clocked and/or synchronized using the controller of the x-ray source. In a diagnosis device with separate nuclear medical and radiographic detectors, this embodiment allows the patient to be moved without interruption from the SPE/SPECT scanner segment into the x-ray segment or vice versa.

Radiation protection curtains or covers are preferably arranged on the diagnosis device in order to protect the operating personnel.

It should finally be noted that the described embodiment of the diagnosis device with a tumor treatment device is preferable, nevertheless other embodiments of apparatus for therapies, which require anatomical and functional imaging at the same time as easy patient accessibility, are likewise possible. By way of example, a perfusion of the myocardial muscle can be determined by way of the nuclear examination and an anatomical assignment can be carried out at the same time by way of the radiographic examination of the corresponding coronary vessels, and a corresponding balloon dilation is derived therefrom and a stent or stem cells are introduced. With these applications, the diagnosis device is designed with the appropriate apparatus to implement the treatment.

The advantages achieved with the invention thus particularly consist in the good anatomical imaging by means of the radiographic examination, combined with the functional imaging with the display of the metabolism by means of the nuclear medical examination which can be fused in a short amount of time and with high registration precision, with a good accessibility to the patient additionally being provided for instance for a tumor therapy.

BRIEF DESCRIPTION OF THE DRAWINGS

Exemplary embodiments of the invention are described in more detail below with reference to the figures, in which.

Corresponding parts are each provided with the same reference characters in the different figures.

DETAILED DESCRIPTION OF THE INVENTION

Figure 1:
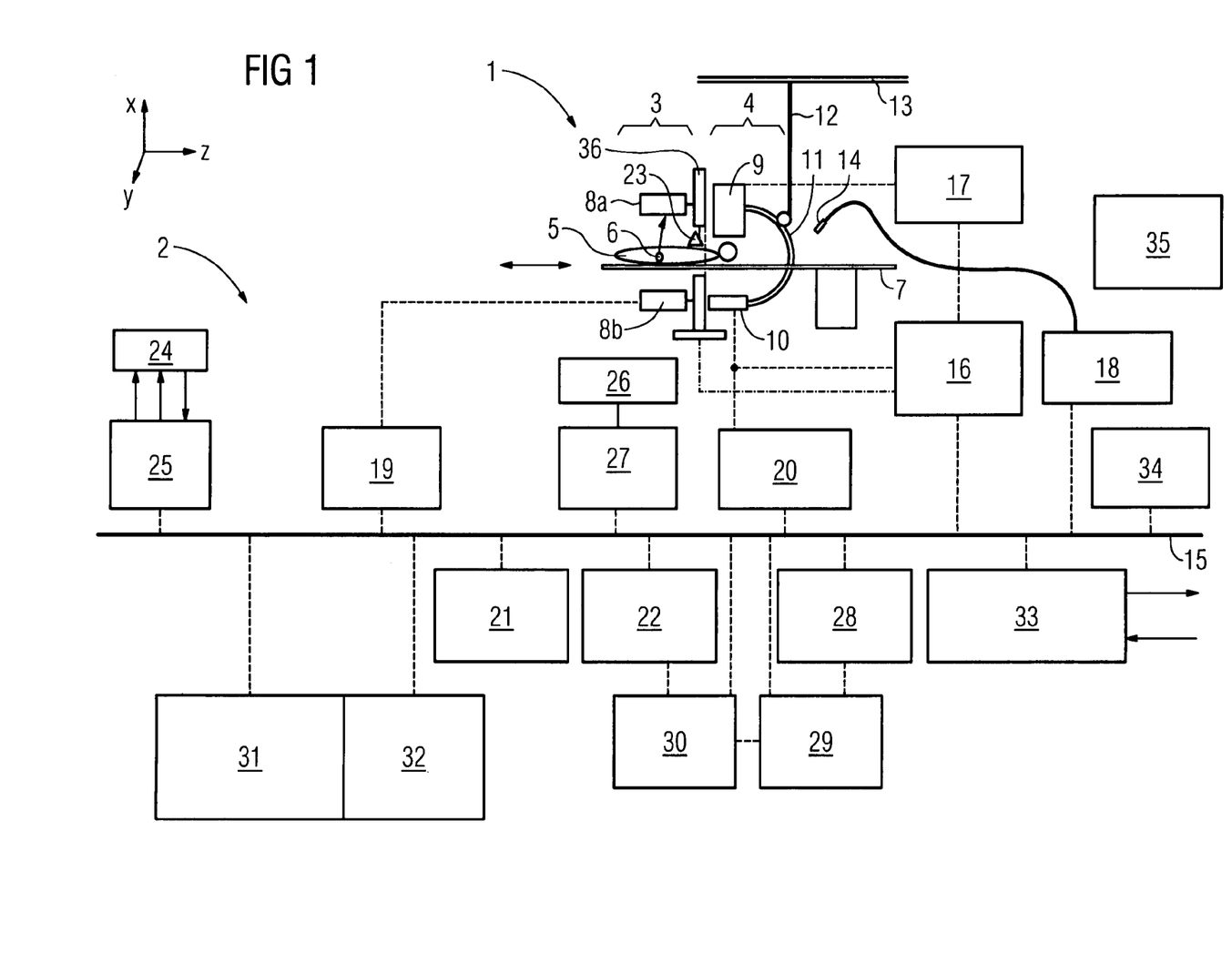
FIG. 1 shows a schematic representation of a first exemplary embodiment of an inventive diagnosis device.

FIG. 1 shows a schematic representation of a first exemplary embodiment of an inventive diagnosis device 1 with the block diagram structure of an evaluation and/or control device 2.

The diagnosis device 1 comprises a first measurement area 3 for recording SPE or SPECT images and a second measurement area 4 for recording x-ray images. A patient 5 administered with radiopharmacs containing radioactive materials prior to the examination, which accumulate in a tumor as a tracer 6, is moved by means of a patient bed in the form of support 7, which can be moved in the Z-direction, for an examination, firstly through the first measurement area 3 and then through or into the second measurement area 4.

The first measurement area 3 comprises an SPE or SPECT measuring head, which is designed in FIG. 1 as two opposing detector arrays 8a, b which are aligned to one another. The detector arrays 8a, b each comprise a collimator (not shown in further detail), which operates as a directional filter and/or as a scattered radiation filter for gamma radiation emitted from the tracer. The detector arrays 8a, b have a plurality of quanta detectors, which are designed as semiconductor detectors or photo multipliers having scintillation and/or converter layers arranged upstream thereof.

The second measurement area 5 has a radiation source 9 in the form of an x-ray source as well as an x-ray detector 10 for detecting x-rays emitted by the x-ray source 9. The radiation source 9 and the x-ray detector 10 are arranged on the free end segments of a C-arm 11, which is linked to a frame 13 in a moveable manner by way of a stand 12, so that by rotating the C-arm 11, the x-ray source 9 and the x-ray detector 10 can be guided around the reclining patient 5 in a circular path.

Furthermore, an ablation catheter 14 is provided, which can be inserted into the patient reclining in the diagnosis device 1 for treatment purposes.

The evaluation and control device 2 is connected to a plurality of modules via a data bus 15, said modules being described below:

The data bus 15 is connected to a system controller 16, which comprises a first output for controlling the x-ray detector 10, a second output for controlling the detector array 8a, b, and a third output for controlling a high voltage generator 17 for supplying the x-ray source 9.

The data bus 15 is also connected to an ablation device 18, which controls the ablation catheter 14.

Starting from the detector arrays 8a, b, a further signal path leads to the data bus 15 via an SPE/SPECT preprocessing module 19. A corresponding signal path likewise leads from the x-ray detector 10 to the data bus 15 via an x-ray and preprocessing module.

The data bus 15 is connected to an image processing unit for SPE/SPECT images 21 and to an image processing unit for x-ray images 22, with the data processing for soft tissue x-ray images (DynaCT) also being carried out in the latter.

A movement sensor system 23 is provided on the diagnosis device 1 to record patient movements during the examination, said movement sensor system 23 being linked to the data bus 15 by way of an interface 24 and a movement and gating processor 25. Furthermore, physiological sensors can be attached to the patient 5, said sensors supplying signal data in a module for physiological signal processing 27 by way of an interface 26. In particular, ECG, pulse, respiration and blood pressure data is received and further processed in the module 27. The results of the signal processing and/or the signal data are fed into the data bus 15 by the module 27.

In an image fusion and reconstruction unit 28, the SPE/SPECT data and the x-ray images/soft tissue x-ray images are merged and transferred in a combined display. An image correction unit 29 is provided to compensate for patient movements and physiological changes in the patient during the examination. In addition, a calibration unit 30 is integrated in the evaluation and control device 2.

The results of the examination are displayed in a display unit 31, on which the SPE/SPECT x-ray images or combined images can be displayed on a monitor for instance. Furthermore, operating and control data can be displayed for the diagnosis device 1, in particular for the ablation device 18. A human-machine interface 32 serves to manually control the diagnosis device 1, in particular the SPE/SPECT, the x-ray system and the ablation device 18. A DICOM interface 33 for communicating with a network for transmitting patient data and image data as well as an image and data storage device 34 are provided for further processing and documentation of the examination results and of the treatment process. The diagnosis device 1 also comprises voltage supply units 35 for supplying the individual modules.

Figure 2:
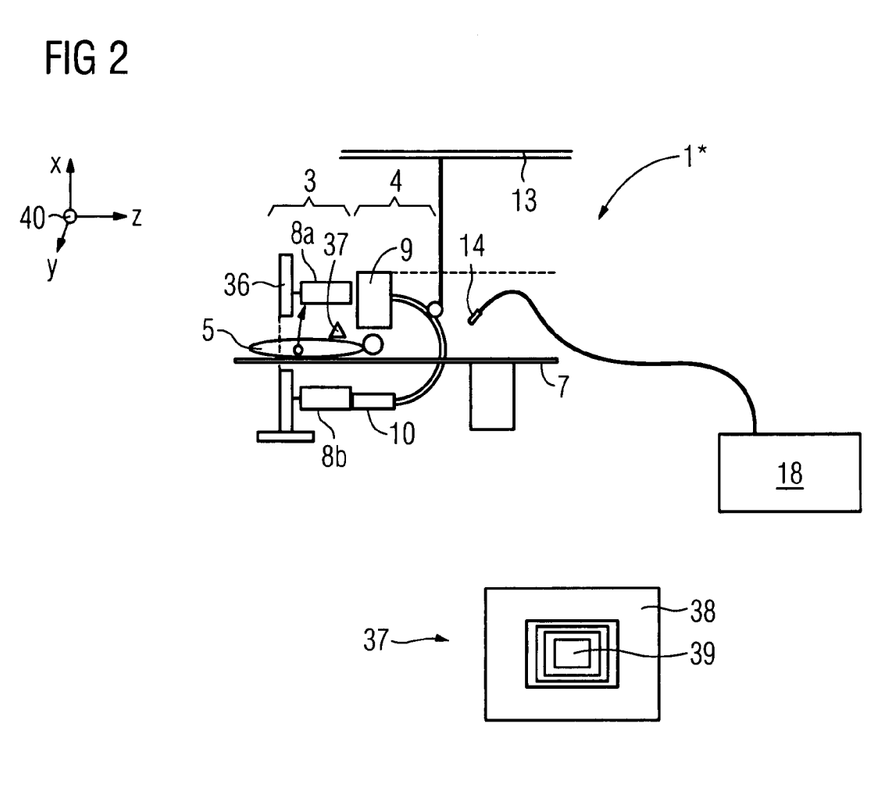
FIG. 2 shows a block diagram of a second exemplary embodiment of an inventive diagnosis device.

Typical examination protocols and/or workflows for the diagnosis device 1 in FIG. 1 are specified below:
Workflow 1:
Tracer injection into the patient 5
Optional x-ray contrast agent injection into the patient 5
X-ray examination (preferably soft tissue x-ray examination)
SPECT examination (e.g. of the whole body)
Workflow 2:
Tracer injection into the patient 5
Optional x-ray contrast agent injection into the patient 5
SPECT examination (e.g. of the whole body)
X-ray examination (preferably soft part x-ray examination, in particular in an organ region determined by the SPECT examination as affected.
Workflow 3 with minimally invasive therapy:
Tracer injection into the patient 5
Optional x-ray contrast agent injection into the patient 5
SPECT examination (e.g. of the whole body)
X-ray examination (preferably soft x-ray examination, in particular in the organ region determined by the SPECT examination as affected)
Insertion of the ablation catheter 14 using x-ray control
Ablation of the tumor tissue
Monitoring the ablation using x-ray recordings
Workflow 4 with high-resolution prerecordings and with minimally invasive therapy:
High-resolution prerecordings using CT or MRI (sent and/or received by way of the DICOM interface)
Repositioning the patient 5 in the diagnosis device 1
Tracer injection into the patient 5
Optional x-ray contrast agent injection into the patient 5
SPECT examination (e.g. of the whole body)
"Software based registration" and fusion of the 3D prerecordings (CT, MRI) with the SPECT recordings
X-ray examination (preferably soft tissue x-ray examination in particular in the organ region determined by the SPECT examination as affected), with a minimal resolution but more up-to-date data than the prerecording
Insertion of the ablation catheter 14 using x-ray control
Ablation of the tumor tissue
Monitoring the ablation using x-ray recordings The upper region of FIG. 2 shows a modified embodiment of the diagnosis device 1 in FIG. 1. The diagnosis device 1* in FIG. 2 has a diaphragm 36, which, in contrast to the embodiment in FIG. 1, is arranged in front of the detector arrays 8a, b and the x-ray source 9 and the x-ray detector 10 arranged downstream thereof. With the diagnosis device 1*, both the first and also the second measurement area 3 and/or 4 are located on a common side of the diaphragm 36. An RFID transponder plaster 37 is affixed to the patient 5, said RFID transponder plaster 37 consisting of a plaster 38 and/or a carrier material which can be affixed to human skin and the actual RFID transponder 39 in accordance with the magnification in the lower region of FIG. 2. An RFID position sensor receiver 40 is provided to pinpoint the RFID transponder plaster 37 and thus also the precise position and movement of the patient 5, which feeds its measurement values into the data bus 15 (cf. FIG. 1.)

Figure 3:
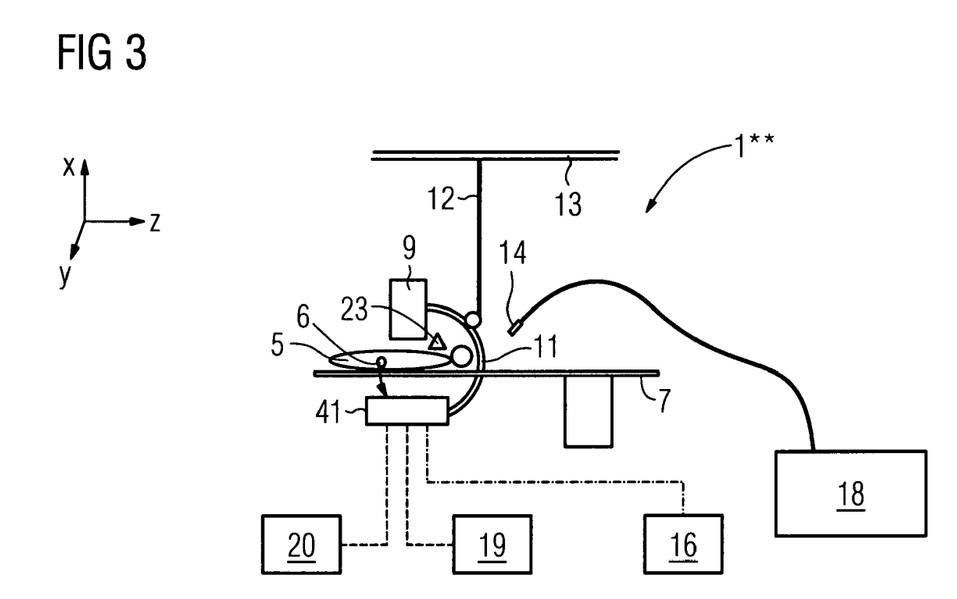
FIG. 3 shows a schematic representation of a third exemplary embodiment of an inventive diagnosis device.

FIG. 3 shows a third embodiment of an inventive diagnosis device 1, which differs from the diagnosis device 1 in FIG. 1 in that the functions of the detector arrays 8a, b (FIG. 1) and the x-ray detector 9 (FIG. 1) are combined in a common detector 41. The detector 41 can register both the x-rays emanating from the x-ray source 9 and also the gamma radiation emanating from the tracer 6 and can thus carry out a simultaneous measurement using both radiation types without changing the patient's position. The detector 41 is preferably designed as a solid body detector, in particular with a flat or essentially flat or only slightly curved detector surface. In the diagnosis device 1 in FIG. 3, the first and second measurement areas 3 and/or 4 of the diagnosis device 1 in FIG. 1 are designed to overlap and/or to be congruent.

Figure 4:
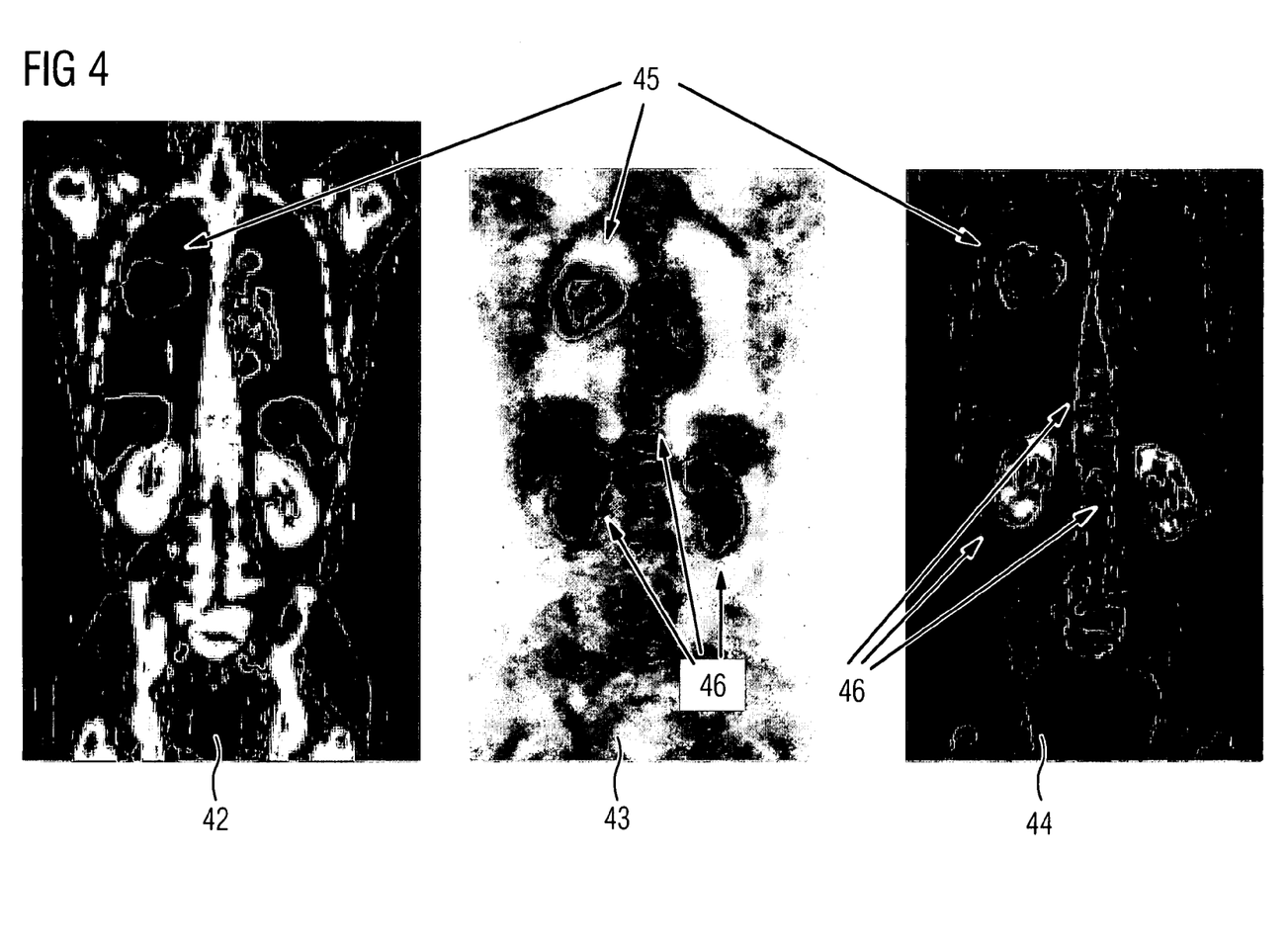
FIG. 4 shows an exemplary embodiment of a data fusion of an x-ray image having a SPECT recording.

FIG. 4 illustrates the fusion of measurement data of a SPECT examination and an x-ray examination. A 2D cross-section of a 3D x-ray soft part image 42 is shown in the left side in FIG. 4 and a SPECT recording 43 of the same region in the body of the patient 5 is shown in the center. These two recordings 42 und 43 have been producing using a diagnosis device according to FIG. 1, 2 or 3. A combined SPECT/x-ray soft part image 44 is shown on the right side, said image 44 comprising the merged measurement data of recordings 42 and 43. The combination or fusion of the measurement data results in a combined image 44, in which primary lung tumors 45 and secondary tumors and metastases 46 can be better and more clearly detected by the treating physicians than in the non-merged images 42 and/or 43.

Figure 5:
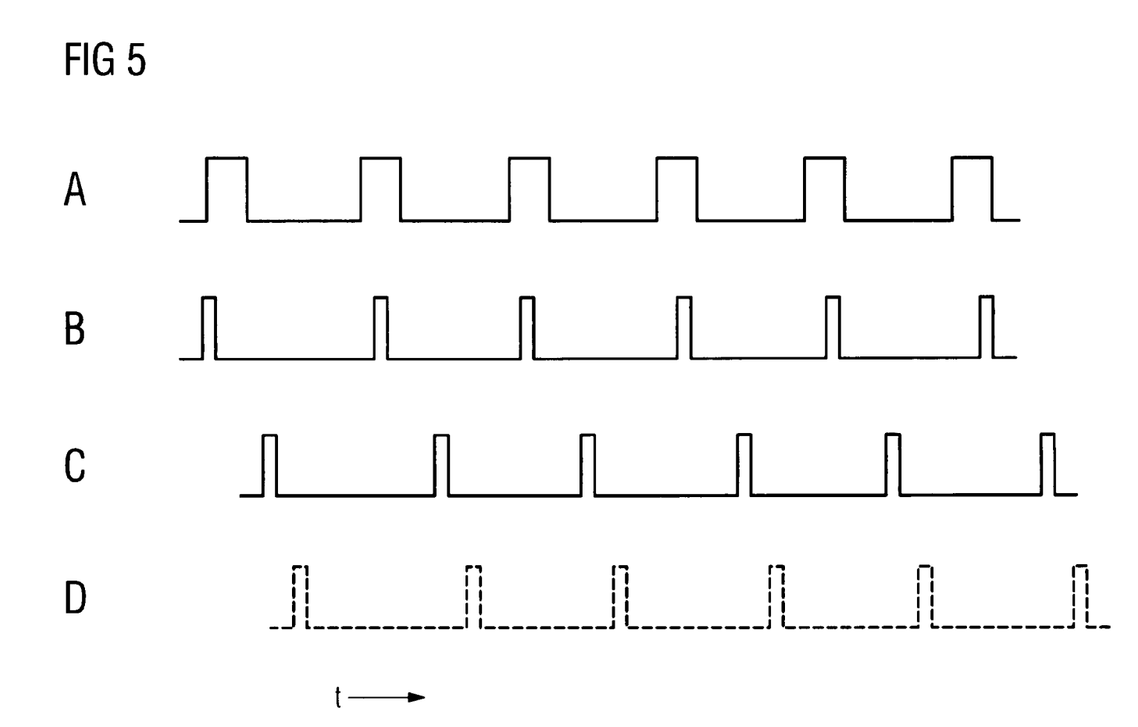
FIG. 5 shows a schematic representation of signal paths to illustrate a clocked readout of the detector system of the exemplary embodiments 1 or 2.

FIG. 5 illustrates a clocked readout of the different sensors in the diagnosis device 1, 1* or 1** of FIG. 1, 2 and/or 3. In the first column, the signal path A for reading out the quanta detectors of the detector arrays 8a, b over time is shown, with the quanta detectors being read out at a high signal level. In the second column, the signal path B for reading out the ECG and the respiration is shown. The third column shows the signal path V for outputting an x-ray pulse by the radiation source 9. A comparison of the signal paths A and B shows how the radiation source 9 is only activated at times at which the quanta detectors are not read out. In this way, mismeasurements by the quanta detectors are avoided. The signal path D relates to the temporal curve of the readout of the x-ray detector 10, which is read out in each instance following an x-ray pulse. The quanta detectors and x-ray detectors are read out alternately and in a non-overlapping fashion. The detector 41 in FIG. 3 can also be controlled in a similar manner, with measurement data relating to the gamma radiation and measurement data relating to the x-rays being read out alternately.

Figure 6:
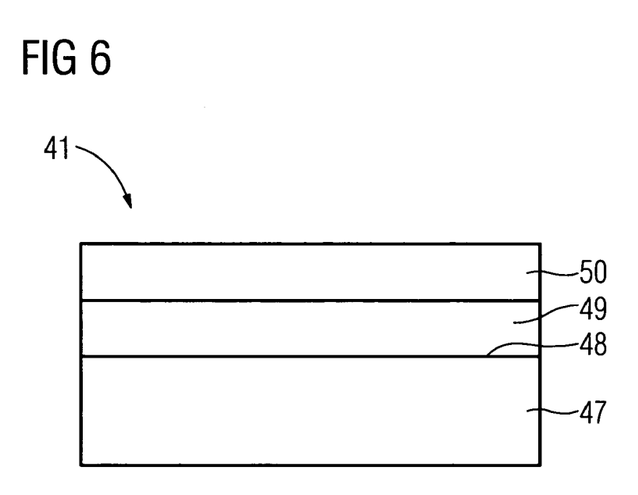
FIG. 6 shows a schematic representation of a detector in FIG. 3.

FIG. 6 shows a schematic representation of the detector 41 in FIG. 3. The detector 41 comprises a sensor matrix or pixel matrix 47, in which are arranged a plurality of individual sensors or pixels in rows and columns. The top side of the sensor matrix or pixel matrix 47 forms the detector surface 48 which is hit by the photons to be measured. Upstream of the sensor matrix or pixel matrix 47 is arranged a converter 49, which converts the high-energy photons, i.e. x-ray quanta or gamma quanta, into low-energy light pulses or electrical charges. A collimator 50 is optionally arranged upstream of the converter 49, said collimator operating as a directional filter or a scattered radiation filter for the incident high-energy photons.

The invention claimed is:

1. A device used in a combinable radiographic medical examination and nuclear medical examination on a patient, comprising:
    a gamma radiation source arranged on a body of the patient;
    an x-ray source that emits an x-ray radiation to the body of the patient;
    a diagnosis device that evaluates the x-ray radiation for the radiographic examination and evaluates the gamma radiation for a single photon emission as the nuclear medical examination,
    wherein the diagnosis device comprises a patient movement sensor system with a movement sensor that derives a patient movement from results of the x-ray and/or gamma radiation examinations and an RFID transponder and sensors externally applied onto the patient,
    wherein the derived patient movement is taken into account to eliminate image artifacts during an image reconstruction; and
    a detector system comprising a detector surface that simultaneously measures the x-ray radiation and the gamma radiation without changing a position of the patient.

2. The device as claimed in claim 1, wherein the detector system records a two-dimensional locally-resolved and object-imaging x-ray projection image.

3. The device as claimed in claim 1, wherein the detector system is a flat panel detector comprising a sensor matrix or a pixel matrix.

4. The device as claimed in claim 3, wherein the flat panel detector is a readout matrix comprising a converter.

5. The device as claimed in claim 4, wherein the converter is arranged upstream of the readout matrix and converts an incident high-energy photon into an electrical charge or into a low-energy light pulse.

6. The device as claimed in claim 1, wherein the detector system comprises a collimator which is a directional filter for a high-energy photon so that only the high-energy photon passes in a projection direction for the nuclear medical examination or for the x-ray projection image.

7. The device as claimed in claim 1,
    wherein the detector system comprises an SPE detector for the nuclear medical examination and an x-ray detector for the radiographic examination, and
    wherein the SPE detector and the x-ray detector are arranged sequentially.

8. The device as claimed in claim 1, wherein the diagnosis device generates a 3-D soft tissue recording by evaluating the x-ray radiation.

9. The device as claimed in claim 1, wherein the nuclear medical examination is a SPECT examination and the radiographic examination is a CT examination or an x-ray examination.

10. The device as claimed in claim 1, further comprising a control unit which controls the device to perform a SPE or SPECT examination, or an x-ray examination, or a combined nuclear and radiographic medical examination.

11. The device as claimed in claim 10, wherein the combined nuclear and radiographic medical examination is performed by overlaying:
    a 2D SPE examination data with a 2D x-ray examination data, or
    a 3D SPECT examination data with a 2D x-ray examination data, or
    a 2D SPE examination with a 3D x-ray examination data, or a 3D SPECT examination data with a 3D x-ray examination.

12. The device as claimed in claim 1, further comprising an integrated tumor treatment device.

13. The device as claimed in claim 1, further comprising:
a patient support system that moves the patient through a measurement area of the diagnosis device, and
a position sensor that records a movement of the patient support system.

14. The device as claimed in claim 1, wherein the x-ray source or the detector system is accommodated on a C-arm construction, or two separate support legs, or an annular gantry.

15. The device as claimed in claim 1, further comprising an integrated ablation device.

16. The device as claimed in claim 1, wherein a measurement data of the nuclear medical examination and the radiographic examination is read out alternately.

17. A method for combining a radiographic medical examination and nuclear medical examination on a patient, comprising:
emitting a gamma radiation from a gamma radiation source arranged on a body of the patient;
emitting an x-ray radiation from an x-ray source to the body of the patient;
evaluating the x-ray radiation for the radiographic examination;
evaluating the gamma radiation for a single photon emission as the nuclear medical examination;
mathematically evaluating the x-ray and/or gamma radiation examinations in conjunction with an RFID transponder and sensors applied externally onto the patient to determine a patient movement during the examinations;
correcting the examination measurement data based on the mathematical evaluation; and
simultaneously measuring the x-ray radiation and the gamma radiation without changing a position of the patient.

18. A diagnosis device used in a combinable radiographic medical examination and nuclear medical examination on a patient, comprising:
a gamma radiation source arranged on a body of the patient;
an x-ray source that emits an x-ray radiation to the body of the patient;
an evaluation device that evaluates the x-ray radiation for the radiographic examination and evaluates the gamma radiation for a single photon emission as the nuclear medical examination;
a patient movement sensor system that mathematically determines a patient movement via analysis of the x-ray and/or gamma radiation examinations in conjunction with an RFID transponder and sensors externally applied onto the patient, wherein the mathematically determined patient movement is taken into account by the evaluation device to eliminate image artifacts during an image reconstruction; and
a detector system comprising a detector surface that measures the x-ray radiation and the gamma radiation without changing a position of the patient.

19. The diagnosis device as claimed in claim 18, wherein the detector system simultaneously or alternately measures the x-ray radiation and the gamma radiation.

* * * * *